US00PP27279P3

(12) United States Plant Patent
Olesen et al.

(10) Patent No.: US PP27,279 P3
(45) Date of Patent: Oct. 18, 2016

(54) ***CLEMATIS* PLANT NAMED 'EVIPO056'**

(50) Latin Name: *Clematis viticella*
Varietal Denomination: Evipo056

(71) Applicants: Mogens Nyegaard Olesen, Fredensborg (DK); Raymond J. Evison, St. Sampsons (GB)

(72) Inventors: Mogens Nyegaard Olesen, Fredensborg (DK); Raymond J. Evison, St. Sampsons (GB)

(73) Assignee: POULSEN ROSER A/S, Fredensborg (DK)

( * ) Notice: Subject to any disclaimer, the term of this patent is extended or adjusted under 35 U.S.C. 154(b) by 131 days.

(21) Appl. No.: 14/121,279

(22) Filed: Aug. 15, 2014

(65) Prior Publication Data

US 2016/0050830 P1 Feb. 18, 2016

(51) Int. Cl.
*A01H 5/02* (2006.01)

(52) U.S. Cl.
USPC ..... Plt./228

(58) Field of Classification Search
USPC ..... Plt./228
See application file for complete search history.

(56) References Cited

PUBLICATIONS

Perfection by Poulsen—*Clematis*—Main Varieties, 2013 (3 pgs totoal).*

* cited by examiner

*Primary Examiner* — Susan McCormick Ewoldt

(57) ABSTRACT

A new *Clematis* plant with a compact growth habit, profuse, pink flowers, and continuous summer flowering. The variety successfully propagates from softwood cuttings and is suitable for cultivation in commercial nursery culture. This new and distinct variety has shown to be uniform and stable in the resulting generations from asexual propagation from vegetative cuttings.

2 Drawing Sheets

Botanical classification: Genus: *Clematis*. Species: *viticella*.

Variety denomination: 'Evipo056'.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling.

The two parents were crossed during the summer of 1998 and the resulting seeds were planted the following winter in a controlled environment in Guernsey, Channel Islands, United Kingdom. The new variety named 'Evipo056' originated as a single seedling from the stated cross.

The new *clematis* plant may be distinguished from its female seed parent and male pollen parent by the following characteristics. The seed parent has light pink flowers, while the new variety has pink flowers. The pollen parent variety has a flower diameter of 70 to 80 mm while the new variety has flowers from 80 to 100 mm.

The objective of the hybridization of this *clematis* plant was to create a new and distinct variety for nursery culture with unique qualities such as:

1. Uniform and abundant pink flowers;
2. Vigorous and compact growth, making the variety suitable for container culture; and
3. Improved disease resistance.

This combination of qualities was lacking in *clematis* plants that were in commercial cultivation and the qualities have been substantially achieved in the new variety.

'Evipo056' was selected by Mogens N. Olesen and Raymond J. Evison in their *clematis* development program in the Channel Islands, United Kingdom in 1998. Asexual reproduction of 'Evipo056' by means of vegetative cuttings and traditional layering was first performed by Mogens N. Olesen and Raymond J. Evison in the nursery during the summer of 1999. This initial and subsequent asexual propagations have demonstrated that the characteristics of 'Evipo056' are true to type and are transmitted from one generation to the next.

BRIEF DESCRIPTION OF THE DRAWING

The accompanying color illustrations show as true as is reasonably possible to obtain in color photographs of this type the typical characteristics of the buds, flowers, leaves, and stems, of 'Evipo056'.

Specifically illustrated in FIG. 1 of the drawings are open flowers on a branch, flower upon opening, flower reproductive parts detached, and a seed head.

Figure 1:
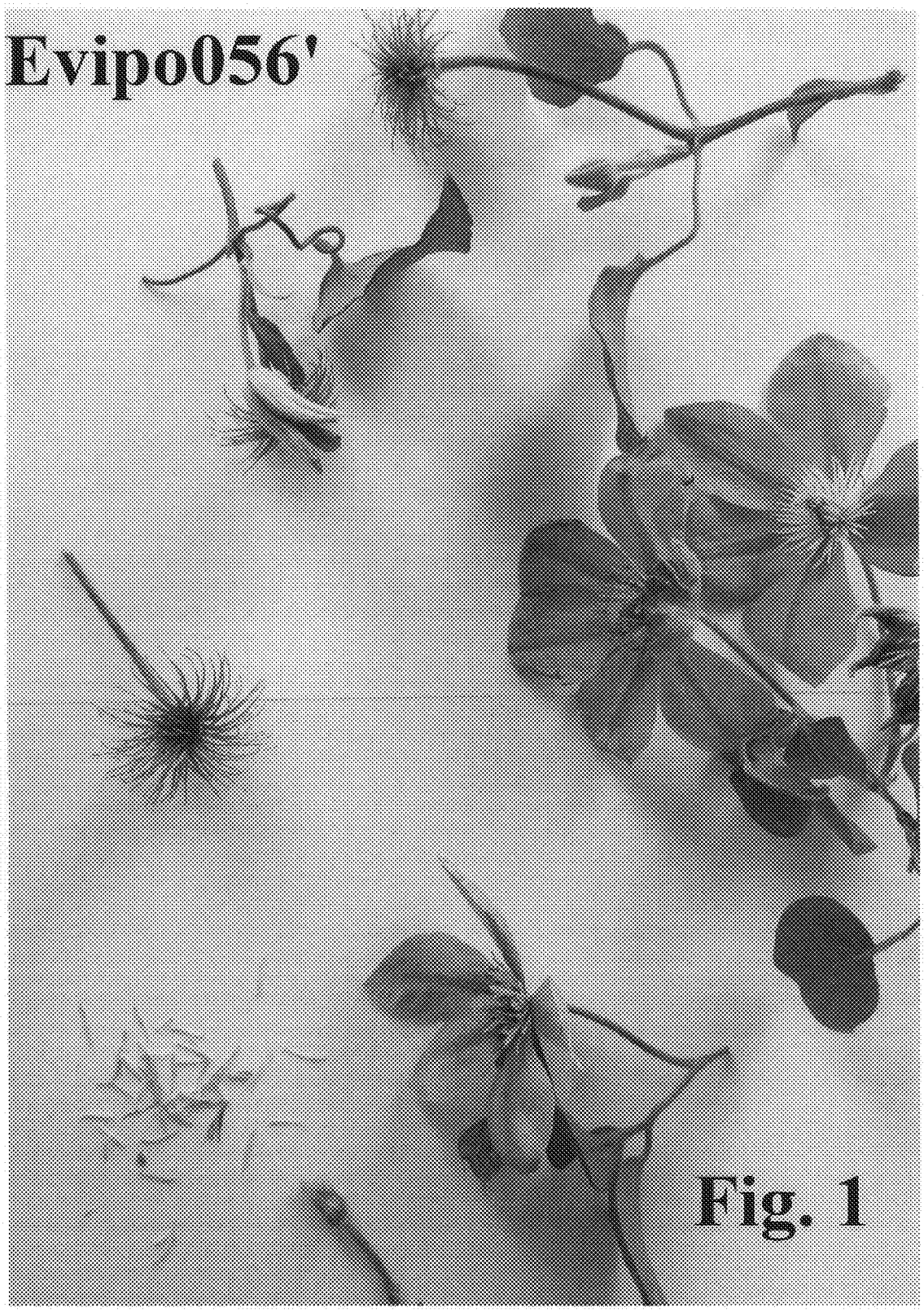
Figure 2:
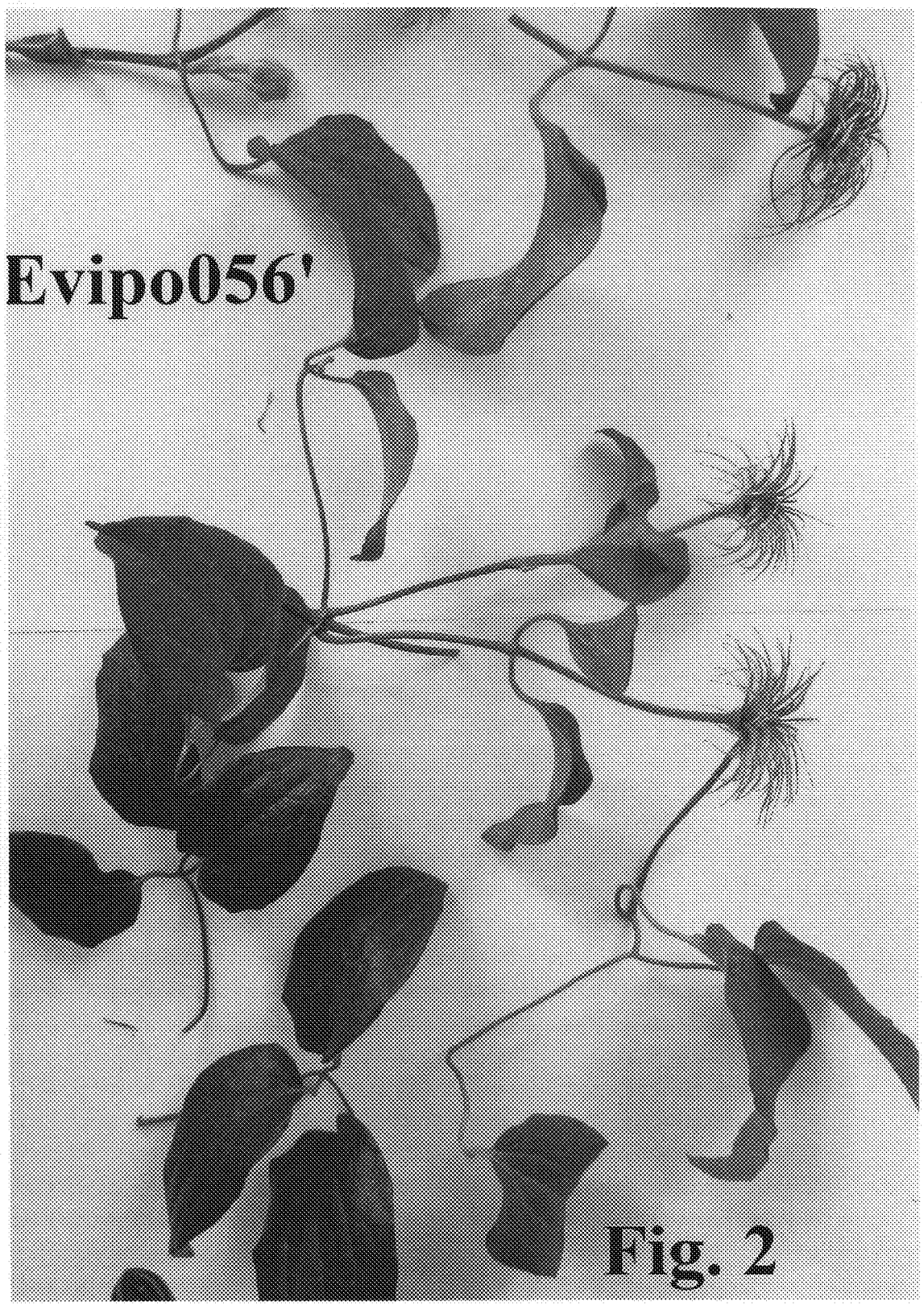
FIG. 2 shows mature leaves, stems, and seed heads.

Plants shown are 2 years of age.

DETAILED DESCRIPTION OF THE VARIETY

The following is a detailed description of 'Evipo056', as observed in its growth throughout the flowering period in Fredensborg Denmark. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *clematis* variety 'Evione' described and illustrated in U.S. Plant Pat. No. 10,222 issued Feb. 3, 1998 are compared to 'Evipo056' in Chart 1.

CHART 1

| | 'Evipo056' | 'Evione' |
|---|---|---|
| Flower diameter | 80 to 100 | 13 to 18 cm |
| Tepal upper surface after opening | Purple-Violet Group 82C with a central stripe Purple-Violet Group 81A | Purple Group 76A with a central bar Red-Purple Group 71A |
| Tepal count | 6 | 6, sometimes 8 |

Flower and Flower Bud

Blooming habit: Continuous. The natural flowering period is generally from April to September.

Flower bud:

*Size*.—Normally 20 mm in length. Bud diameter is 10 mm.

*Bud form*.—Elliptic.

*Bud color*.—At ¼ opening tepals are Purple-Violet Group 80A.

Peduncle:

*Surface texture*.—Smooth.

*Length*.—On average 25 mm.

*Color*.—Yellow-Green Group 146C.

*Strength*.—Moderately strong.

Receptacle:

*Surface texture*.—Lightly pubescent.

*Shape*.—Broad funnel.

*Size*.—2 mm (h)×4 mm (w).

*Color*.—Yellow-Green Group 146C.

Flower arrangement:

*Location on vine*.—New growth only.

*Borne*.—Singly.

*Attitude*.—Flower orientation is horizontal and somewhat upward facing.

Flower bloom:

*Size*.—On average, flowers are 80 to 100 mm in diameter and 15 mm in depth.

*Profile*.—Open flowers are flat.

*Fragrance*.—None.

*Lasting quality*.—Flowers normally remain up to 10 days on the plant.

Tepals:

*Tepal color*.—Upon opening, the upper surface is Purple-Violet Group 80A. The lower surface is Purple-Violet Group 82B with a central streak of Green-Yellow 1B. After opening, the upper surface is Purple-Violet Group 82C with a central stripe Purple-Violet Group 81A. The lower surface is Purple-Violet Group 82D with a central streak of Green-Yellow 1D.

*Quantity*.—Normally 6 tepals.

*Size*.—50 mm in length by 25-40 mm wide.

*Shape*.—Individual tepal shape is elliptic. The tepal apex is mucronate. The tepal base is typically acute.

*Apex recurvature*.—Slightly curved.

*Tepal cross section*.—Slightly reflexed.

*Margins*.—Entire.

*Persistence*.—Tepals drop off cleanly.

*Tepal overlap*.—Tepals overlap slightly.

Reproductive organs:

*Pollen*.—None observed.

*Anthers*.—Size: 5 mm in length. Color: Yellow Group 2B. Quantity: On average, 60.

*Filaments*.—Color: Yellow Group 2D. Length: 10-15 mm.

*Pistils*.—Quantity: On average, 60.

*Stigmas*.—Superior in location relative to the length of the filaments and the height of the anthers.

*Styles*.—Color: Yellow-Green Group 144B. Length: 12 mm.

Seed head characteristics:

*Size*.—30 mm in height. 40 mm in diameter.

*Quantity*.—The average number of seeds produced per seed head is 60.

*Style appearance*.—Plumose, semi-erect.

Plant

Plant form: Climbing.

Growth: Moderate.

Size: Seasons growth attains 100 to 150 cm in height. Average spread is 50 cm.

Stems:

*Color*.—Juvenile stems are Yellow-Green Group 146B. Mature stems are Greyed-Purple Group 183B.

*Internodes*.—8 to 13 cm between nodes.

*Length*.—Normally 50 cm from the base of the plant to the flowering portion of the stem.

*Diameter*.—Normally 2 mm.

*Texture*.—Mature stems are ribbed.

Plant foliage:

*Leaf characteristics*.—Deciduous.

*Arrangement*.—Trifoliate.

*Leaf size*.—Compound leaves are normally 120 to 150 mm (l)×120 to 240 mm (w). Leaflets are normally 50 to 85 mm (l)×35 to 45 mm (w).

*Abundance*.—On average 2 leaves per 10 cm of stem.

*Leaf color*.—Juvenile upper Yellow-Green Group 146B. Juvenile lower Yellow-Green Group 146C. Mature upper Yellow-Green Group 147A. Mature lower Yellow-Green Group 147B.

*Stipules*.—Absent.

*Petioles*.—Size: Normally 40 to 80 mm in length by 1 to 2 mm diameter. Texture: Lightly pubescent. Color: Greyed-Purple Group 183A and Yellow-Green Group 146C.

*Petiolule*.—Size: Normally 15 to 45 mm in length by 1 to 2 mm diameter. Texture: Lightly pubescent. Color: Greyed-Purple Group 183A and Yellow-Green Group 146C.

*Leaflet shape*.—Generally elliptic. The base is rounded. The apex is acute. Margin: Entire. Surface: The upper and lower sides are somewhat rough. Thickness: Moderate. Glossiness: Not glossy.

Disease resistance: Subject to any disease that normally attacks the species. However the variety is more tolerant to *clematis* wilt, *Ascochyta clematidina*, than some *clematis* known to the inventors.

Cold hardiness: The variety is tolerant to USDA Hardiness Zone 6.

Heat tolerance: The variety has been found to be suitable for climate conditions found in the American Horticulture Society heat zone 7.

We claim:

1. A new and distinct variety of *clematis* plant named 'Evipo056', substantially as described and illustrated, due to its abundant pink flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *